Figure 1:
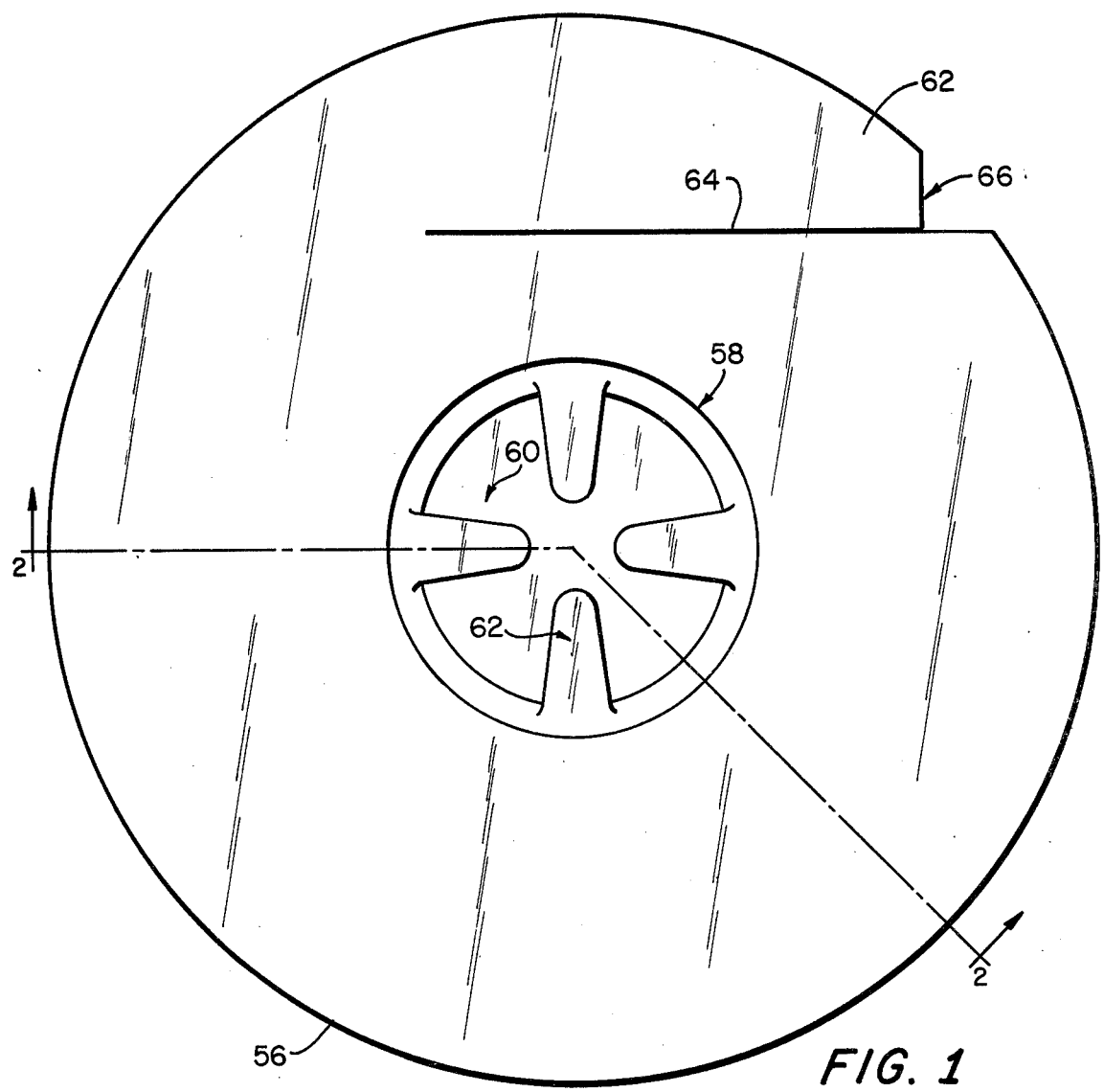

United States Patent [19]

Wilson

[11] 4,166,456
[45] Sep. 4, 1979

[54] CARRIER RELEASE SHEET

[75] Inventor: Ronald Wilson, Lunenburg, Mass.

[73] Assignee: Vaughn Corporation, Salisbury, Mass.

[21] Appl. No.: 840,108

[22] Filed: Oct. 6, 1977

Related U.S. Application Data

[63] Continuation-in-part of Ser. No. 760,099, Jan. 17, 1977.

[51] Int. Cl.$^2$ .............................................. A61B 5/04
[52] U.S. Cl. ................................ 128/640; 128/803
[58] Field of Search ............. 128/2.06 E, 2.1 E, 404, 128/417, 418, DIG. 4; 206/210

[56] References Cited

U.S. PATENT DOCUMENTS

| | | | |
|---|---|---|---|
| 3,581,736 | 6/1971 | Zenkich | 128/2.06 E |
| 3,685,645 | 8/1972 | Kawaguchi | 128/417 X |
| 3,702,613 | 11/1972 | Panico | 128/417 |
| 3,805,769 | 4/1974 | Sessions | 128/2.06 E |
| 3,828,766 | 8/1974 | Krasnow | 128/2.1 E |
| 3,865,099 | 2/1975 | Robichaud | 128/2.1 E |
| 3,882,853 | 5/1975 | Gofman et al. | 128/2.06 E |
| 3,989,035 | 11/1976 | Zuehlsdorff | 128/2.1 E |
| 4,029,086 | 6/1977 | Corasanti | 128/2.06 E |
| 4,050,453 | 9/1977 | Castillo | 128/2.06 E |
| 4,079,731 | 3/1978 | Danby | 128/2.06 E |
| 4,082,086 | 4/1978 | Page et al. | 128/2.06 E |

FOREIGN PATENT DOCUMENTS 2274264  1/1976  France .................................. 128/2.06 E

*Primary Examiner*—Lee S. Cohen
*Attorney, Agent, or Firm*—Schiller & Pandiscio

[57] ABSTRACT

An improved carrier release sheet is described for use with biopotential skin electrodes of the type including a stud, a pad preloaded with an electrically conductive material and in electrical contact with the stud, a base sheet having an aperture and secured to said stud so that the pad is exposed through the aperture to one side of the base sheet having an adhesive coating. The carrier release sheet includes a cylindrical cavity of an improved configuration for receiving the preloaded pad of the electrode in a noncontacting relationship and a tab integrally formed with the remainder of the carrier release sheet so as to enable quick and easy release of the carrier sheet from the adhesive coating.

15 Claims, 2 Drawing Figures

CARRIER RELEASE SHEET

RELATED APPLICATIONS

This application is a continuation-in-part of my copending application Ser. No. 760,099 filed Jan. 17, 1977.

This invention relates to electrodes and more particularly to carrier release sheets for medical or biopotential skin electrodes.

Biopotential skin electrodes are well known for detecting potentials from the skin of a living body. Generally two or more electrodes are placed on the body at selected locations dependent on the type of potentials being measured, and the potential differences are recorded or monitored on appropriate electronic instruments. For example, these electrodes can be used to monitor and record cardiopotentials from the chest and limbs, while electroencephalograms can be provided from appropriate positions on the scalp.

In recent years many of these electrodes have been made inexpensively so that they can be disposed of after use. Examples of these electrodes are shown and described in U.S. Pat. Nos. 3,610,229; 3,696,807; 3,701,346 and 3,820,531 as well as my copending application Ser. No. 760,099 filed Jan. 17, 1977. Typically, these electrodes include an electrically-conductive paste or gel and designed so taht it can be secured to an electrical connector which, in turn, is in electrical contact with testing or monitoring instruments. In some disposable electrodes, the reservoir includes a porous pad preloaded with the electrically conductive paste or jel for electrically connecting the stud to the skin of the living body. (See for example U.S. Pat. Nos. 3,610,229 and 3,701,346). In order to attach the electrode to the skin, the stud and pad are usually suitably secured to a base sheet. The base sheet typically is in the form of tape having an adhesive layer which contacts the skin so as to hold the pad and more particularly the gel within the pad in electrical contact with the skin.

This disposable-type electrode also usually is provided with a carrier release sheet, removable just prior to use, in order to prevent the gel from exposure to the air and thus prematurely drying. The carrier release sheet is typically made of an air impermeable opague or translucent strippable material, such as stiff paper or a plastic material coated with a release agent, such as silicone, and secured to the adhesive surface of the base sheet in contact with the pad.

Very often people have experienced some difficulty initially separating the release sheet from the base sheet so as to completely remove the latter from the former in one piece in order to expose the gel and adhesive layer of the base sheet. This may result in tearing the base sheet or the base sheet folding with a portion of the adhesive layer contacting another portion making it difficult to separate. Another problem arises with certain carrier release sheets that are designed to contact the pad since the pads have a tendency to peel away with the release sheets when the latter are removed from the base sheet. In addition, mishandling and rough treatment of these electrodes can result in separation of the stud from the base sheet, exhaustion of some or all of the gel from the pad, or otherwise damage of the pad, all of which may make the electrode dysfunctional. Because some carrier release sheets are opaque such defects are often not detectable until the removal of the base sheet from the carrier release sheet.

One particular carrier release sheet, shown and described in U.S. Pat. No. 3,701,346, includes a raised center portion formed as a cylinder, the inner diameter of which is substantially the same as the outer diameter of a cup member of the electrode which supports a pad preloaded with an electrically-conductive gel. The height of the cylindrical center portion is greater than the combined height of the cup member and the pad. The base of the center portion has a centrally located, inwardly-directed, conical projection which engages the central portion of the pad so as to hold the pad firmly in the cup member in contact with a conductive plate portion which in turn is electrically connected to the stud. The pad thus remains nestled in the cup member and is not peeled away with the carrier when the latter is removed. Although the carrier release sheet of the patented device is constructed so as to have a self-supporting shape so that the center section will not collapse when stored, the conical projection engaging the center of the pad tends to force gel toward the peripheral edges of the pad and into the cup, which may result in the lack of the gel on the skin of the body being tested. Further, any pressure on the stud toward the conical projection due to mishandling and rough treatment can cause damage to the electrode in general and the pad and stud in particular.

It is an object of the present invention therefore to provide an improved carrier release sheet for use with biopotential electrodes which overcomes or minimizes the aforementioned problems of the prior art.

More specifically, objects of the present invention are to provide an improved carrier release sheet for use with a biopotential electrode which does not engage the pad of the electrode during normal storage conditions which will have little tendency to peel off the pad from the electrode when the sheet is peeled from the base sheet, which will provide a minimum exhaustion of the gel from the pad, which can easily be peeled in one complete piece from the base sheet with little chance of damage to the base sheet, and which is preferably transparent to allow and promote visual inspection of the electrode.

These and other objects of the present invention are achieved by an improved carrier release sheet for use with biopotential skin electrodes, particularly those electrodes having a pad preloaded with gel, and a base sheet having an adhesive coating for securing the electrode to a body. The sheet comprises a self-supporting cup-shaped projection having a plurality of ribs (1) spaced from the pad of the electrode when the carrier sheet and electrode are secured together under normal storage conditions and (2) contact a minimal portion of the pad when compressive pressure is applied between the carrier sheet and pad. The carrier sheet is also preferably transparent to allow and promote fully visual inspection as well as integrally formed and provided with a slit, extending across a portion of the sheet and spaced from the cup-shaped projection, so as to provide a tab. The carrier sheet is preferably dimensioned such that the end of the tab extends beyond the edge of the base sheet so that the tab can easily be pulled from the base sheet exposing a portion of the adhesive coating in order that the remainder of the carrier sheet can easily be removed and the electrode can easily be applied.

Other objects of the invention will in part be obvious and will in part appear hereinafter. The invention accordingly comprises the product possessing the features, properties and relation of components which are exemplified in the following detailed disclosure, and the scope of the application of which will be indicated in the claims.

Figure 2:
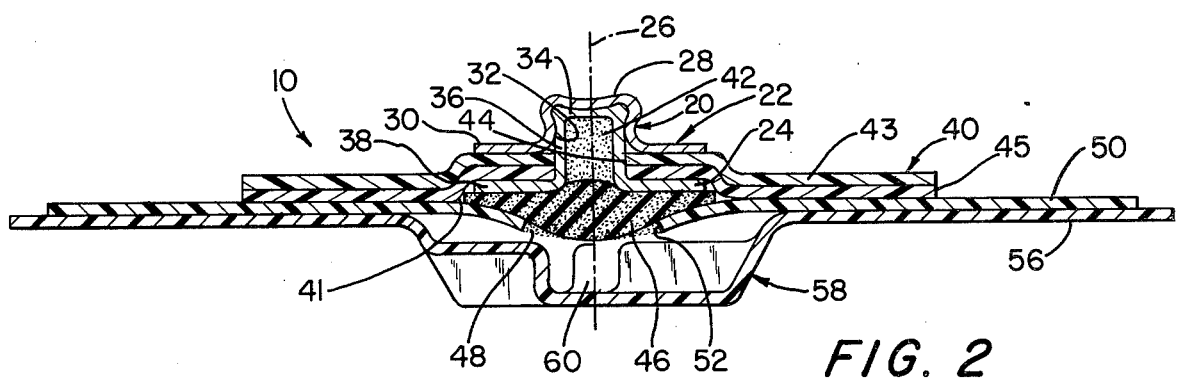

For a fuller understanding of the nature and objects of the present invention, reference should be had to the following detailed description taken in connection with the accompanying drawing wherein:

FIG. 1 is a plan view of the preferred embodiment of the carrier release sheet of the present invention; and FIG. 2 is a cross-section view of the embodiment of FIG. 1 taken along line 2—2 of FIG. 1 as used with the biopotential skin electrode described in my U.S. copending application Ser. No. 760,099.

Referring to the drawing, the biopotential skin electrode assembly 10 is shown and described in detail in my U.S. copending application Ser. No. 760,099. The assembly comprises a stud member 20 including post member 22 and retaining member 24, both being described with respect to an elongated axis of symmetry shown as center line 26. The post and retaining members are made of any one of several materials depending on the particular use to which the electrode is put and the particular electrically conductive gel or paste which is used with the electrode assembly, as described in my U.S. copending application Ser. No. 760,099.

The post member 22 is essentially bulbous-shaped at an extreme end 28 reduced in its center to form a flange or collar 30 at its other end. Collar 30 is of uniform width and thickness and extends entirely around the periphery of the member so that center line 26 passes through the center of and is perpendicular to the collar. Post member 22 is dimensioned so that end 28 can engage in a snap fit relationship with a known type of female connector member (not shown) of the electrical monitoring or recording equipment being used. The end of post member 22, provided with collar 30, is also provided with a cavity 32.

The retaining member 24 is essentially tubular shaped, being bulbous-shaped at one extreme end 34 and reduced at its center 36 to form a flange 38 at its other end. Flange 38 also is of a uniform width (being substantially of the same diameter as collar 30) and thickness and extends around the periphery of the retaining member so that center line 26 passes through the center of and is normal to flange 38. The retaining member 24 is dimensioned so that the bulbous-shaped end 34 can engage in the cavity 32 of the post member 22 in a snap-fitting relationship so that the collar 30 of post member 22 is spaced by a predetermined distance from the flange 38 of retaining member 24 with the center 36 of the retaining member forming a substantially cylindrically-shaped extension of reduced diameter (i.e., of less diameter than the diameter of either the flange or collar) therebetween.

The annular space or groove formed between collar 30 and flange 38 is adapted to receive and retain a flat sheet of material 40, the latter being described in greater detail hereinafter. A reservoir or well 42 is formed by the interior tubular portion of the retaining member 24 wherein the well is centrally-disposed in the end of the retaining member adjacent sheet 40. Sheet 40 is cupped around the periphery of flange 38 so as to form a pocket 41. Pocket 41 and well 42 are adapted to receive the electrically-conductive gel or paste so as to provide an electrically-conductive column or path between the patient's skin and the stud. Pocket 41 and well 42 are designed so as to preferably form a somewhat cylindrical recess which extends into the bulbous-shaped end 34 of post member 22 so that the center axis of this recess approximately coincides with the center axis 26. The outer peripheral edge of the well 42 is preferably flared or chamfered to improve the structural integrity of the stud as well as provide a greater area in which the gel or paste may be dispensed.

Stud 20 is implaced centrally in a center aperture 44 of the flat sheet 40, the latter preferably being substantially circular or elliptical in shape. Sheet 40 is preferably made of a stretchable material or materials which are transparent to light as well as impervious to the gel or paste retained in pocket 41 and well 42 so as to help preserve the gel. One particular construction of sheet 40 which is satisfactory is a laminated assembly including under layer 45 secured in any known manner, such as with a suitable adhesive to the overlayer 43. The thickness of sheet 40 is made slightly greater than the distance between the collar 30 and flange 38 so that the sheet is slightly compressed at assembly, when the retaining member 24 is snap-fitted into post member 22 and is retained or secured in the groove between the collar and flange. Sheet 40 is disposed so that it is centered with the axis 26 and the plane of the layer is oriented substantially perpendicular to the center axis 26.

The electrode assembly also includes a thin porous compressible disc or pad 46 preferably made of an absorbent material such as an opened-cell foamed polyurethane or the like. The pad has a diameter which is approximately the same as the diameter of the pocket 41 and flange 38 and is centrally placed in the pocket 41 over flange 38 substantially coaxial with the axis 26, so as to substantially cover the reservoir 42. The thickness of the pad in an uncompressed state is larger than the depth of pocket 41 so that at least the center portions of the pad extend beyond the undersurface of sheet 40.

The reservoir 42 and pad 46 are preferably preloaded with an electrically-conductive paste or gel 48, such as conventionally used with electrographic instruments, and depending upon the type of stud 20 utilized, the gel may, for example, comprise a sodium chloride salt dissolved in a solution of, for example, agar with other constituents providing desired predetermined values of conductivity, pH, viscosity and the like. Alternatively, a chloride-free gel can be employed, when for example, a stainless steel stud is used.

The electrode assembly further includes a flat base sheet 50, substantially coaxially secured with respect to axis 26 and preferably cut in a substantially circular or elliptical pattern so that the diameter of base sheet 50 is larger than and overlaps the layer 42. The sheet 50 is made of a flexible, stretchable, porous, light transparent material that is provided on one side thereof with an adhesive coating and includes a centrally located aperture 52.

In accordance with the present invention the pressure-sensitive adhesive coating of base sheet 50 as well as pad 46 may be protected when not in use by an improved water impervious transparent strippable carrier release sheet 56. The release sheet is preferably self-supporting and made of a hardened thermoplastic sheet material such as the copolyester extruded film manufactured under the trademark KODAR A 150 by Island Extrusion Corp. of Island Park, N.Y. and typically is about 15–20 mm in thickness. With this type of thermoplastic material each sheet 56 can be heated and stamped pressed into the desired configuration and subsequently allowed to cool. It will be appreciated that alternatively, other materials can be used, such as polyvinyl butyrate formed in the desired configuration by vacuum methods well known in the art.

At least the surface of the release sheet 56 which contacts the adhesive layer is treated with a release agent, such as silicone, so as to provide easy release between the two without adversely affecting the adhesive layer, and preserving the high visual acquity of the release sheet for total device inspection.

The release sheet 56 is preferably provided with the cup shaped cavity 58 for receiving and protecting the pad 46 exposed through aperture 52 of base sheet 50. The cavity is shaped so that pad 46 and release sheet 56 do not touch under normal storage conditions prior to use.

The cavity is preferably in the form of a cylindrically-shaped well having a bottom surface 60 and ribs 62, each of the latter extending radially from the wall of the cavity toward but spaced from the axial center of the cavity which is located approximately coaxially with center axis 26. The ribs remain spaced from the pad under normal storage conditions and are designed to cushion the pad 46 when sufficient pressure is placed between the electrode and release sheet. Specifically, when such pressure is provided the ribs provide relatively minimal contact at the peripheral portions of the pad so as to tend to prevent the exhaustion of gel from the pad. The ribs are preferably equianagularly spaced around the axial center of the cavity with three or four ribs typically being adequate.

The carrier release sheet is also provided with suitable means for providing quick and reliable release of the release sheet 56 from the adhesive layer of the base sheet 50. More specifically, a slit 64 is formed from an edge of a portion of the carrier sheet 56 extending only a portion of the way across the sheet so as to form a tab 62. The tab is secured to an area of the base sheet which is smaller than the remaining portion of the base sheet. For example, where the sheet is formed as a circular or elliptical-shaped disk with the cavity 58 centrally located as shown, the slit 64 extends from the peripheral edge along a chordal segment of the disc about two-thirds of the distance. The sheet may also be provided with the notch 66 formed at the end of the tab. The carrier release sheet is dimensioned so that it completely covers the adhesive layer of the base sheet. At least a portion and preferably the end of the tab 62 at notch 66 extends beyond the edge of the base sheet so that the carrier release sheet can be easily and quickly removed from the base sheet by grasping and holding the base sheet and carrier sheet near the notch 66 and tab 62 and pulling the tab 62 from the base sheet. Since the tab covers a smaller portion of the base sheet, the probability of the carrier release sheet splitting in two or more parts is greatly reduced. Further, the electrode stays with the remaining portion of the release sheet making it easier to apply with less nuisance attributable to the base sheet 50 folding over its adhesive layer.

The invention thus described provides an improved carrier release sheet for use with biopotential skin electrodes which does not engage the preloaded gel pad during normal storage conditions, which will have little tendency to peel off the pad from the electrode when the release sheet is peeled from the base sheet, which will tend to provide a minimum exhaustion of gel from the pad when mishandled, which can easily be peeled from the base sheet with little chance of damage to the electrode, and which can easily be inspected for gross defects throughout the product.

Since certain changes may be made in the above product without departing from the scope of the invention herein involved, it is intended that all matter contained in the above description or shown in the accompanying drawing shall be interpreted in an illustrative and not in a limiting sense.

What is claimed is:

1. In combination with a biopotential skin electrode of the type including a stud, a reservoir of electrically-conductive material in electrical contact with said stud, a base sheet secured to said stud so that said reservoir is exposed to one side of said base sheet, and an adhesive coating disposed on said one side of said base sheet, an improved carrier release sheet supporting said electrode, said carrier release sheet comprising:
a unitary, water impervious, substantially self-supporting sheet (1) having a slit formed across a portion of said self-supporting sheet so as to form a tab and (2) dimensioned so as to completely cover said one side of said base sheet including said adhesive coating and having a portion of said tab extending beyond the peripheral edge of said base sheet with said tab covering a smaller portion of said adhesive coating than the remaining portion of said self-supporting sheet covers so that said self-supporting sheet seals said electrically-conductive material in said reservoir from the surrounding air and so that said self-supporting sheet is easily removable from said adhesive coating by pulling said tab relative to said adhesive coating.

2. The combination in accordance with claim 1 wherein the portion of said tab extending beyond the peripheral edge of said base sheet is the end of said tab, said tab being notched at said end.

3. The combination in accordance with claim 1 further including a cylindrical projection formed in said self-supporting sheet covering said reservoir when said sheet is secured to said adhesive coating.

4. The combination in accordance with claim 1 wherein said self-supporting sheet is substantially transparent.

5. In combination with a biopotential skin electrode of the type including a stud, a pad preloaded with an electrically conductive material and in electrical contact with said stud, a base sheet secured to said stud so that at least a portion of said pad is exposed to one side of said base sheet and an adhesive coating disposed on said one side of said base sheet, an improved carrier release sheet supporting said electrode, said carrier release sheet comprising:
a unitary, substantially water impervious, self-supporting sheet including a cylindrical shaped projection receiving said pad in a non-contacting relationship with said self-supporting sheet being secured to the adhesive coating, said projection including a plurality of inwardly directed ribs dimensioned and oriented with respect to one another so as to be spaced from said pad under normal storage conditions and to contact relatively small portions of said pad when said pad is forced toward said ribs.

6. The combination in accordance with claim 5, wherein the cylindrical axis of said cylindrical projection is substantially coaxially aligned with said pad when said self-supporting sheet is secured to said adhesive coating, said ribs being radially directed toward and spaced from said cylindrical axis.

7. The combination in accordance with claim 6 wherein said ribs are equiangularly spaced around said cylindrical axis.

8. The combination in accordance with claim 7 wherein said projection includes four of said ribs.

9. The combination in accordance with claim 5, wherein said self-supporting sheet is substantially transparent.

10. In an improved biopotential skin electrode of the type including a stud, a pad preloaded with an electrically conductive material and in electrical contact with said stud, a base sheet having an aperture and secured to said stud so that at least a portion of said pad is exposed through said aperture to one side of said base sheet, and an adhesive coating disposed on said one side of said base sheet, an improved carrier release sheet supporting said electrode, said carrier release sheet comprising:

a unitary, water impervious substantially self-supporting sheet including a tab integrally formed to the remaining portion of said self-supporting sheet and a cylindrically shaped projection receiving said pad in a noncontacting relationship, said self-supporting sheet being dimensioned so as to completely cover said one side of said base sheet including said adhesive coating and having a portion of said tab extending beyond the peripheral edge of said base sheet with said tab covering a smaller portion of said adhesive coating than said remaining portion covers so that said carrier release sheet seals said pad from the surrounding air and so that said self-supporting sheet is easily removable from said adhesive coating by pulling said tab relative to said adhesive coating.

11. In the electrode assembly of claim 10 wherein said carrier release sheet further comprises a release coating on at least the side of said self-supporting sheet receiving said adhesive coating.

12. In the electrode assembly of claim 10 wherein said self-supporting sheet is substantially transparent.

13. A carrier release sheet for supporting a biopotential skin electrode, said release sheet comprising a unitary, substantially water impervious, self-supporting sheet including (a) an integrally formed well having a center axis and formed so as to include a plurality of inwardly-directed ribs extending from the sides of said well toward said center axis and (b) a slit formed across a portion of said self-supporting sheet so as to form a tab, said tab forming a smaller portion of said self-supporting sheet than the remaining portion of said self-supporting sheet.

14. A carrier release sheet in accordance with claim 13, wherein said ribs are equiangularly spaced around said center axis.

15. A carrier release sheet in accordance with claim 14, wherein said well includes four of said ribs.

* * * * *